US011931780B2

(12) United States Patent
Riegner, III et al.

(10) Patent No.: US 11,931,780 B2
(45) Date of Patent: Mar. 19, 2024

(54) BOTTLE CLEANER

(71) Applicant: ALTELLE PTE. LTD., Singapore (SG)

(72) Inventors: Rudolf W. Riegner, III, San Diego, CA (US); Selamat B. Ismail, Johor Bahru (MY); Mohd Nasir B. Lazim, Johor Bahru (MY); Syah Izzaideen B. Yusoff, Johor Bahru (MY); Wan Muhamad Nur Zikri B Mat Daud, Johor Bahru (MY)

(73) Assignee: ALTELLE PTE. LTD., Singapore (SG)

( * ) Notice: Subject to any disclaimer, the term of this patent is extended or adjusted under 35 U.S.C. 154(b) by 563 days.

(21) Appl. No.: 17/235,295

(22) Filed: Apr. 20, 2021

(65) Prior Publication Data

US 2021/0331218 A1 Oct. 28, 2021

Related U.S. Application Data

(60) Provisional application No. 63/015,110, filed on Apr. 24, 2020.

(51) Int. Cl.
*B08B 9/42* (2006.01)
*B08B 9/08* (2006.01)
(Continued)

(52) U.S. Cl.
CPC ............ *B08B 9/423* (2013.01); *B08B 9/0852* (2013.01); *B08B 9/283* (2013.01); *B08B 3/02* (2013.01);
(Continued)

(58) Field of Classification Search
CPC ....... B08B 9/423; B08B 9/283; B08B 9/0852; B08B 3/02; B08B 2203/007; B08B 2203/027; B08B 2230/01
(Continued)

(56) References Cited

U.S. PATENT DOCUMENTS 5,421,353 A * 6/1995 Jakubowski ......... A61C 17/036
134/186
9,782,803 B2 10/2017 Semans et al.
(Continued)

FOREIGN PATENT DOCUMENTS

CN 105195481 A 12/2015
KR 100624841 B1 9/2006

OTHER PUBLICATIONS

CN105195481A—machine translation (Year: 2015).*

*Primary Examiner* — Tinsae B Ayalew
(74) *Attorney, Agent, or Firm* — JCIP; Joseph G. Chu; Jeremy I . Maynard

(57) ABSTRACT

A bottle cleaner includes a housing defining a chamber therein. A support frame is disposed within the housing to support one or more bottles. A base is disposed below the housing. A bottom liner is at least partially received within the housing. The bottom liner defines a plurality of openings and a fluid reservoir. At least one pump is disposed within the base to pump liquid from within the fluid reservoir to one or more spray jets for cleaning the bottles. Further, a blower and heater are disposed within the base. The blower discharges air into the chamber through the plurality of openings to dry the bottles. A heater element produces steam which aids in steam sterilization functionality.

14 Claims, 9 Drawing Sheets

(51) Int. Cl.
 *B08B 9/28* (2006.01)
 *B08B 3/02* (2006.01)
(52) U.S. Cl.
 CPC ... *B08B 2203/007* (2013.01); *B08B 2203/027* (2013.01); *B08B 2230/01* (2013.01)
(58) Field of Classification Search
 USPC .......................................................... 134/198
 See application file for complete search history.

(56) References Cited

U.S. PATENT DOCUMENTS

| | | | |
|---|---|---|---|
| 2004/0123885 A1* | 7/2004 | Myong | B08B 9/28 |
| | | | 134/179 |
| 2013/0213443 A1* | 8/2013 | Garcia | A61L 2/07 |
| | | | 134/99.2 |
| 2014/0150830 A1* | 6/2014 | Semans | B08B 3/04 |
| | | | 134/108 |

* cited by examiner

BOTTLE CLEANER

CROSS-REFERENCE TO RELATED APPLICATION

The present application claims the right of priority to U.S. Provisional Patent Application No. 63/015,110 having a filing date of Apr. 24, 2020, the contents of which are hereby incorporated by reference in their entirety.

FIELD OF THE INVENTION

The present disclosure relates to a cleaning device for bottles.

BACKGROUND TO THE INVENTION

Baby bottles must generally be both cleaned and sterilized before use. A common method is to wash the bottles in detergent first and then place the bottles in a sterilizer. Steam sterilizers are one option. Such devices generally comprise a housing which is filled with steam in order to sterilize the bottles and their component parts.

The present invention relates to a device aimed at providing both the ability to clean, sterilize, and dry baby bottles in the same device. The invention is aimed at providing a compact and easy to use device for the purpose of washing, sterilizing, and drying bottles in a single housing.

SUMMARY OF THE INVENTION

According to one aspect of the present invention there is provided a bottle cleaner comprising:
- a housing defining a chamber therein;
- a support frame disposed within the housing to support one or more bottles;
- a base disposed below the housing;
- a bottom liner at least partially received within the housing, the bottom liner defining a plurality of openings and a fluid reservoir;
- at least one pump disposed within the base to pump liquid from within the fluid reservoir to one or more spray jets for cleaning the bottles; and
- a blower disposed within the base, the blower configured to discharge air into the chamber to dry bottles through the plurality of openings.

Preferably, at least one pump includes a fresh-water pump, a sprinkler pump, and a drain pump.

Preferably, the housing comprises a top cover, a bottom cover and a lid movable relative to the top cover.

In a preferred embodiment, the support frame comprises a tray pillar, a bottom tray disposed around the tray pillar and configured to support the one or more bottles, and a top tray disposed around the tray pillar.

Preferably, the bottom tray comprises a plurality of circular members and a plurality of protrusions extending radially inwards from each circular member.

Preferably, the bottom tray further comprises a plurality of curved members attached to the plurality of circular members, each curved member comprising a plurality of studs 211.

In a preferred embodiment, the bottle cleaner further comprises a central tube receiving liquid from the fluid reservoir, a bottom sprinkler assembly receiving liquid from the central tube, and a top sprinkler assembly receiving liquid from the central tube.

Preferably, the bottom liner further comprises a receptacle that is at least partially received by the base, the receptacle defining the fluid reservoir, and wherein a heater element is received within the receptacle to heat liquid within the fluid reservoir. The heater element produces steam which aids in steam sterilization functionality.

Preferably, the receptacle further defines a hole therethrough to fluidly communicate the receptacle with the pump.

In a preferred embodiment, the base further comprises a waste water outlet port to receive waste liquid from the fluid reservoir, and drain it through a tube into the sink or other drain.

In one embodiment, the base further comprises a waste water tank configured to receive waste liquid from the fluid reservoir, the waste tank slidably received within the base.

Preferably, the bottle cleaner further comprises a liquid tank disposed on the base, the liquid tank supplying liquid to the pump.

Preferably, the bottle cleaner further comprises an awning ring disposed between the support frame and the bottom liner.

In one embodiment, the plurality of openings is circumferentially disposed on the bottom liner.

In another embodiment, the blower includes a heater to increase air temperature and reduce drying time.

BRIEF DESCRIPTION OF THE DRAWINGS

The invention will now be described, by way of example, with reference to the following drawings in which.

DETAILED DESCRIPTION OF PREFERRED EMBODIMENTS

Figure 1:
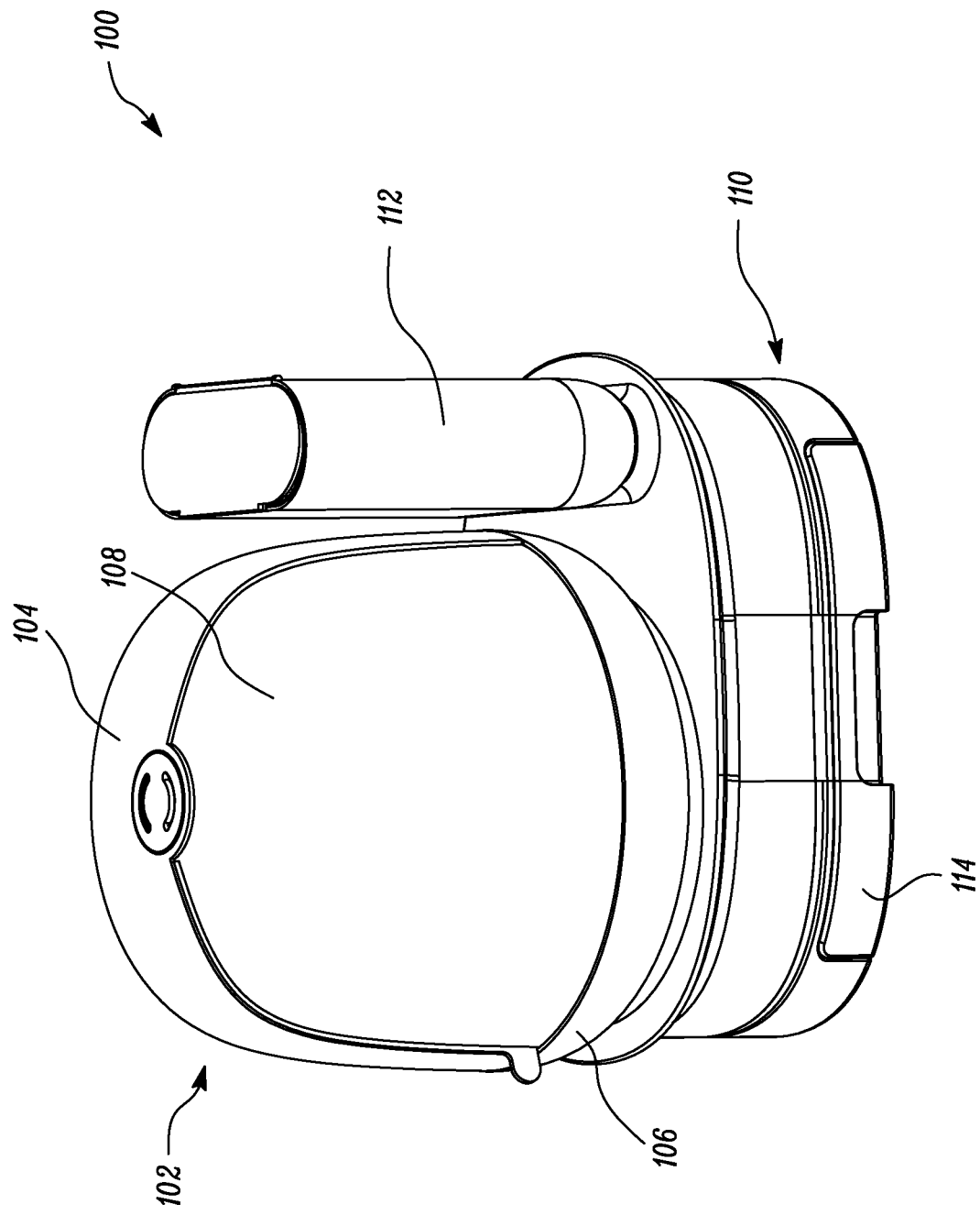
FIG. 1 is a perspective view of a bottle cleaner, in accordance with the present invention.

Referring to FIG. 1, a perspective view of a bottle cleaner 100 is shown. The bottle cleaner 100 may be used for cleaning, sterilizing, as well as drying bottles, such as baby bottles. The bottle cleaner 100 may also be used for cleaning other similar type of utensils or containers.

The bottle cleaner 100 has a housing 102. The housing 102 includes a top cover 104, a bottom cover 106 and a lid 108 movable relative to the top cover 104. The lid 108 may be opened to access inside of the housing 102. A user may open the lid 108 and access the housing 102 to place or retrieve a bottle inside the housing 102. Although it is not shown, the lid 108 may have a handle or any other means through which the user may hold the lid 108. The lid 108 may be pivotable about the top cover 104 about a vertical axis. The housing 102 defines a chamber therein. More specifically, the top cover 104, the bottom cover 106 and the lid 108 together define an internal confined space referred to as the chamber within which the bottle may be placed. The housing 102 may be provided in any suitable shape based on application requirements.

The bottle cleaner 100 further includes a base 110 disposed below the housing 102. The base 110 is illustrated as having a curvilinear shape. The base 110 may be provided with any required shape which may be applicable with various aspects of the present disclosure.

The bottle cleaner 100 includes a liquid tank 112 disposed on the base 110. The base 110 supports various components of the bottle cleaner 100 above and within the base 110. The base 110 may have a substantially hollow structure to adequately house all the required components. The present disclosure is not limited by shape of the base 110 in any manner. Waste liquid flows from the base 110 to a waste water tray 114. The waste water tray 114 is slidably received within the base 110.

Figure 2A:
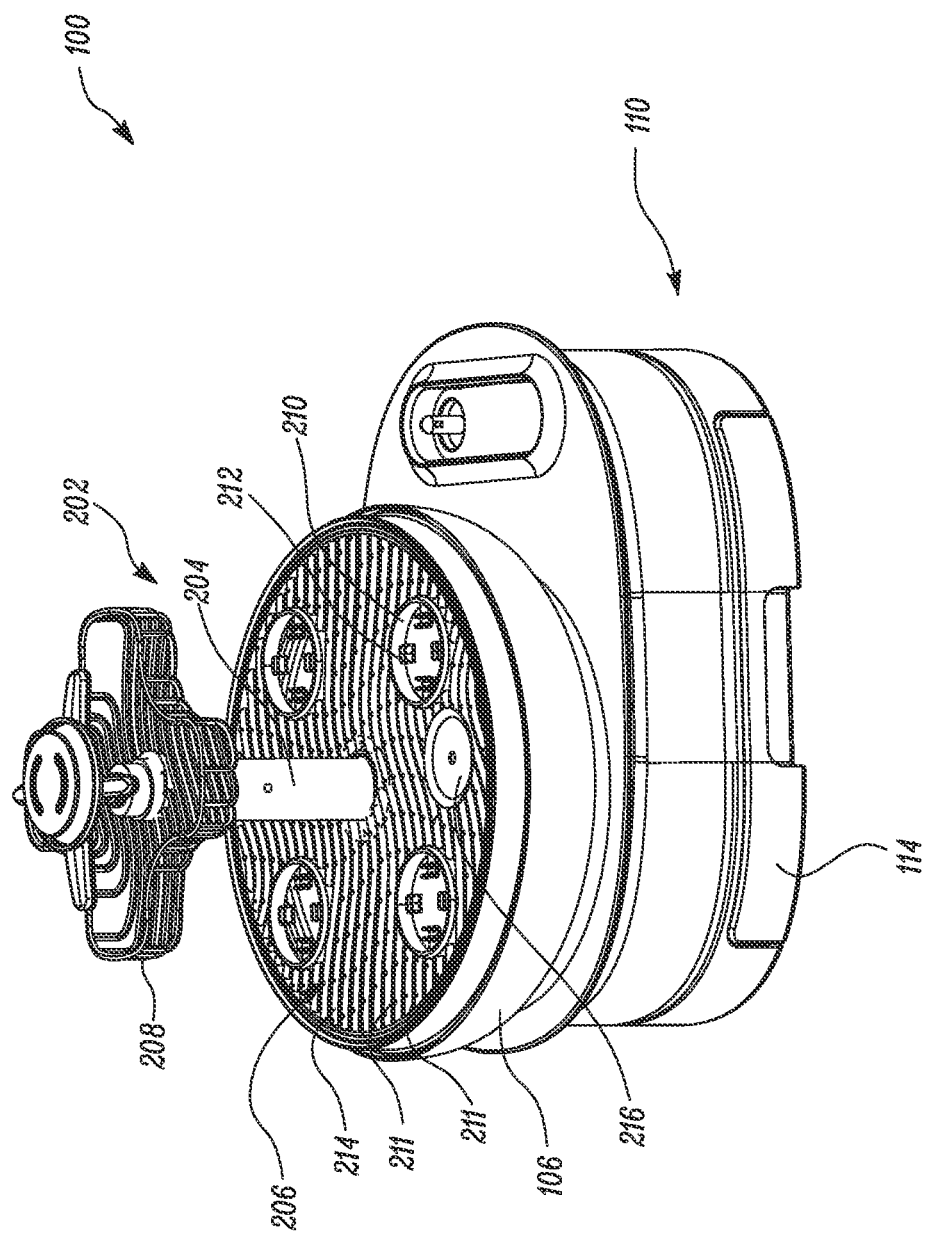
FIGS. 2A and 2B are perspective views of the bottle cleaner without a top cover, in accordance with the present invention.

FIG. 2A shows the bottle cleaner 100 without the top cover 104, the lid 108 and the liquid tank 112. The base 110 defines suitable connection components to couple the liquid tank 112 on the base 110. It should be contemplated that the bottle cleaner 100 is shown without the top cover 104 and the lid 108 to illustrate internal components of the bottle cleaner 100.

The bottle cleaner 100 includes a support frame 202 disposed within the housing 102 to support one or more bottles. The support frame 202 provides overall structural shape and configuration to the bottle cleaner 100 and supports various internal components of the bottle cleaner 100. The support frame 202 includes a tray pillar 204, a bottom tray 206, and a top tray 208. The tray pillar 204 extends in a vertical direction between the bottom tray 206 and the top tray 208. The bottom tray 206 and the top tray 208 are disposed around the tray pillar 204.

The bottom tray 206 is disposed vertically below the top tray 208. The bottom tray 206 is adapted to support one or more bottles. The bottom tray 206 includes a plurality of circular members 210 to support one or more bottles. For each circular member 210, a plurality of protrusions 212 extends radially inwards from the circular member 210 to accommodate different bottle sizes. The bottom tray 206 further comprises a plurality of curved members 214 attached to the plurality of circular members 210. Each curved member 214 includes a plurality of studs 211. Further, the bottom tray 206 is rotatable about the tray pillar 204. Since the bottom tray 206 is rotatable about the tray pillar 204, easy loading of bottles in the bottle cleaner 100 is facilitated. The bottom tray 206 has a generally circular shape.

A number of circular members 210 provided on the bottom tray 206 corresponds to a number of bottles which may be cleaned simultaneously. Further, sizes of the circular members 210 and the protrusions 212 may correspond to sizes of bottles which may be cleaned by the bottle cleaner 100.

The top tray 208 is smaller in size as compared to the bottom tray 206. The top tray 208 may also rotate about the tray pillar 204. The top tray 208 may accommodate smaller components for cleaning, such as bottle cap, nipples, teether etc. The top tray 208 may have a generally cross-shape. The present disclosure is not limited by the structural configurations of the top tray 208 and the bottom tray 206 in any manner.

The bottle cleaner 100 further includes a detergent reservoir 216. The detergent reservoir 216 is defined with the bottom tray 206. The detergent reservoir 216 may be used to add detergent or any other cleaning agent to water being used to clean the water bottles. The detergent reservoir 216 may be placed appropriately on any location on the bottom tray 206.

Figure 2B:
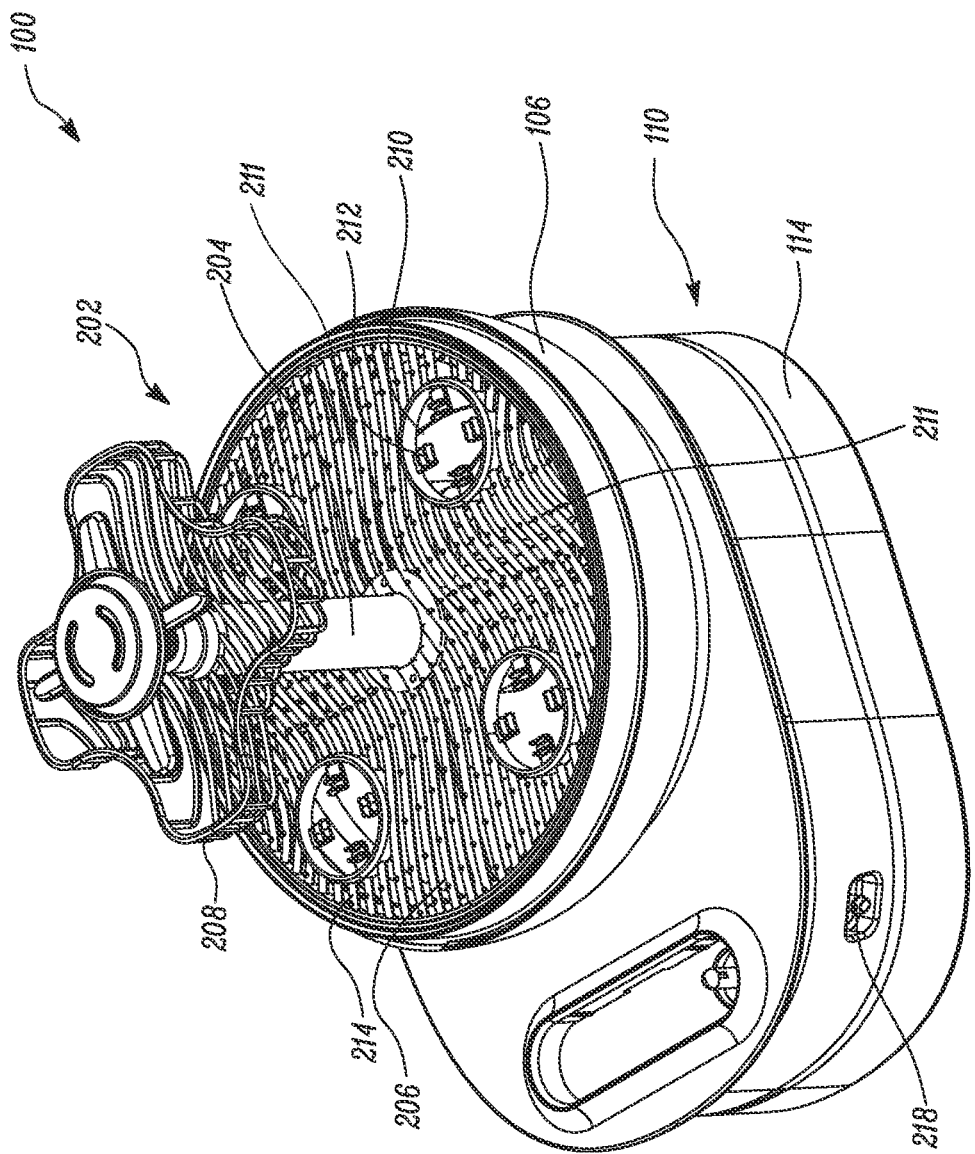

FIG. 2B shows another orientation of the bottle cleaner 100. The bottle cleaner 100 further includes a waste water drainage port 218 to drain waste water through a tube into the sink or other drain. The waste water drainage port 218 is defined by the base 110. The waste water drainage port 218 may be defined at any suitable position on the base 100 as per internal tubing arrangements, as well as placement of a sink, or any other such drainage arrangement.

Figure 3A:
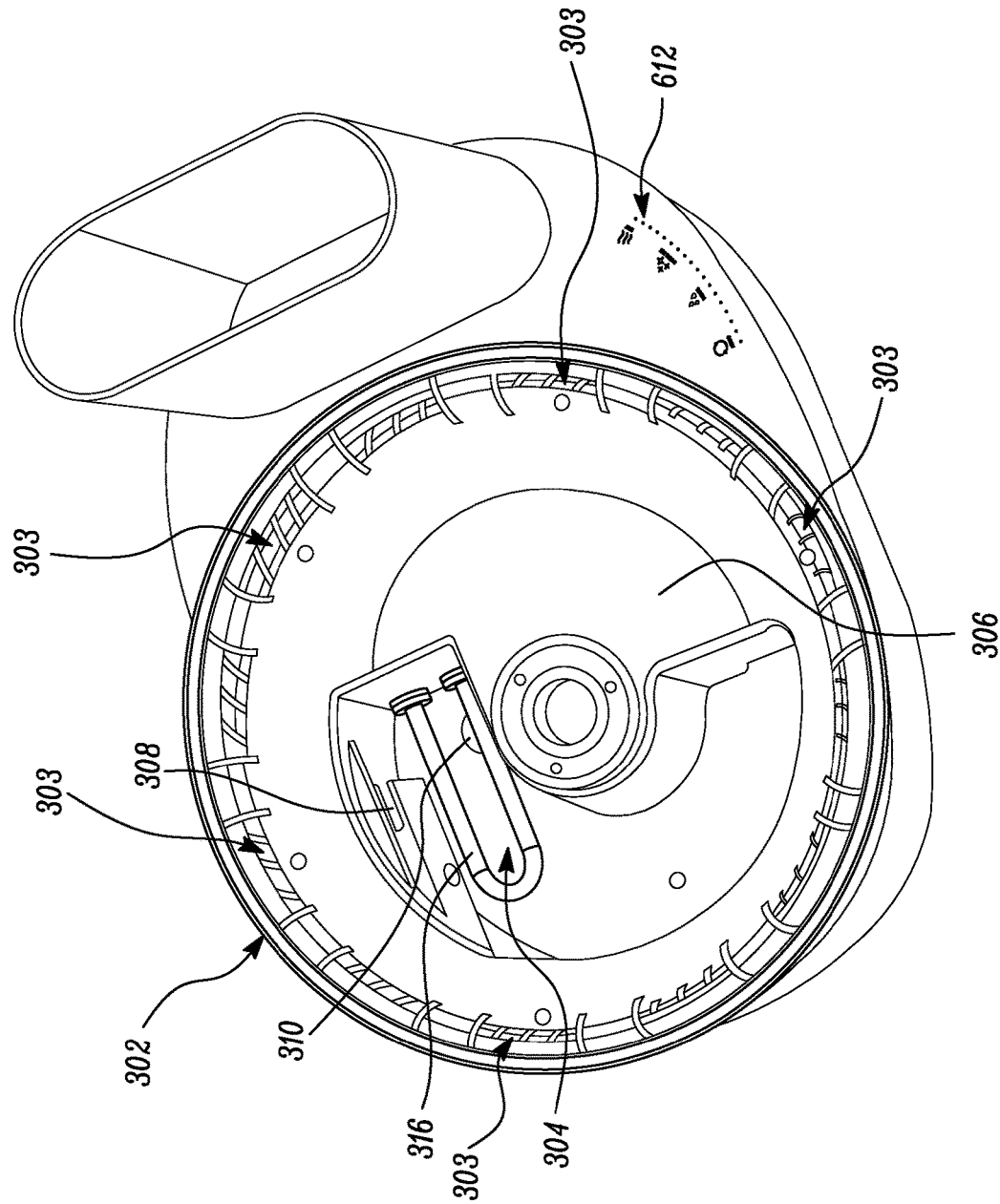
FIGS. 3A and 3B show perspective views of the bottle cleaner without a support frame, in accordance with the present invention.
Figure 3B:
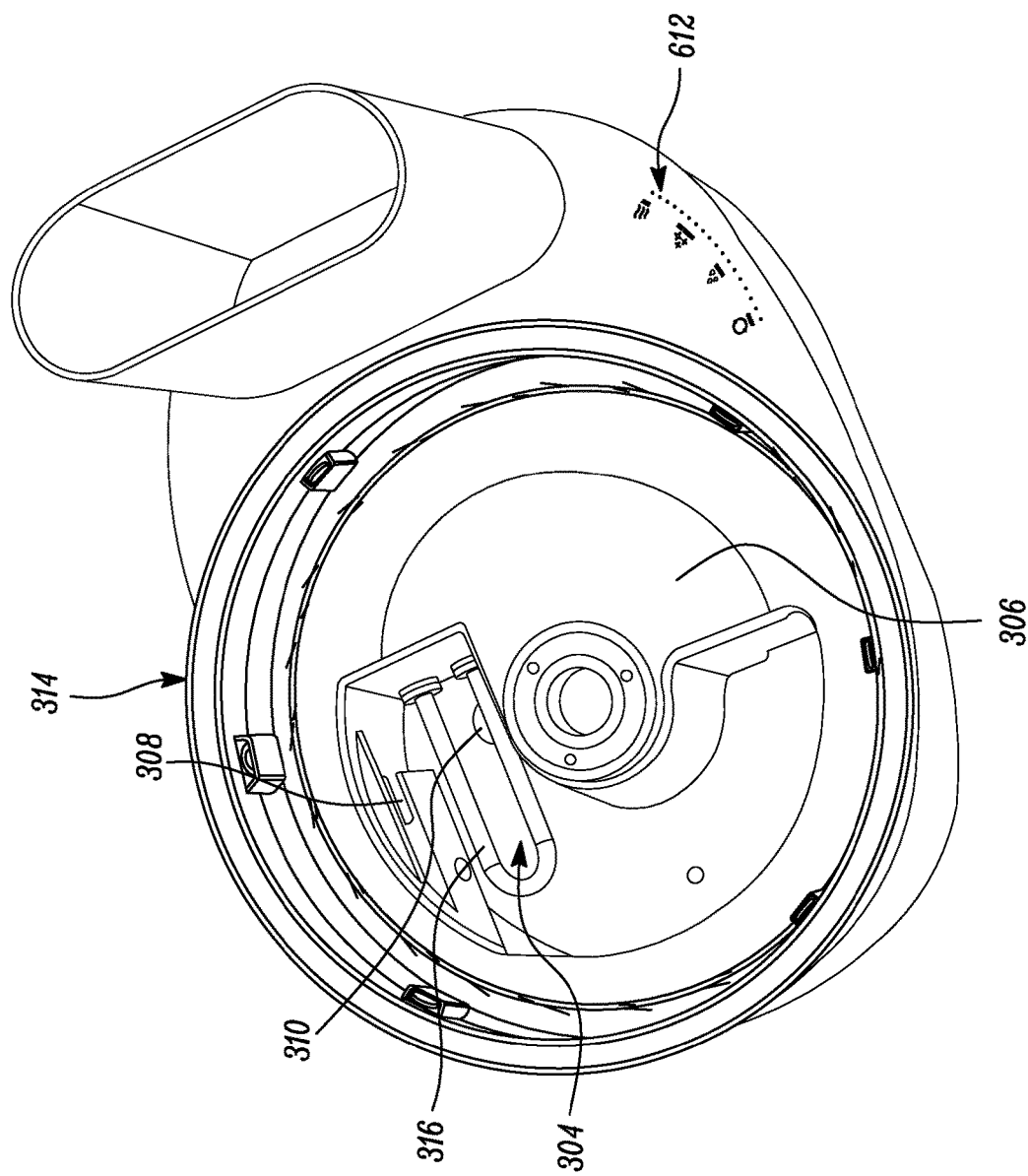

FIGS. 3A and 3B show the bottle cleaner 100 without the tray pillar 204, the top tray 208 and the bottom tray 206. With combined reference to FIGS. 3A and 3B, the bottle cleaner 100 includes a bottom liner 302 at least partially received within the housing 102. The bottom liner 302 defines a plurality of openings 303 and a fluid reservoir 304 therein. The plurality of openings 303 is circumferentially disposed on the bottom liner 302 to direct air within the chamber in a circular flow to dry the bottles. Each opening 303 may be in the form of vents disposed on a circumferential edge of the bottom liner 302. The openings 303 may be arranged in multiple sets with each set including three adjacent openings 303. However, the openings 303 may be arranged in any other manner.

The bottom liner 302 defines a receptacle 306 that is at least partially received by the base 110. The receptacle 306 extends downwards and is received at least partly by the base 110. The receptacle 306 defines the fluid reservoir 304. A heater element 316 is received within the receptacle 306 to heat liquid within the fluid reservoir 304. The heater element 316 is provided to heat water within the receptacle 306 for cleaning bottles and to heat water beyond boiling point such that steam is created. The heater element 316 may aid in generating steam to help during a sterilizing phase of operation of the bottle cleaner 100.

The receptacle 306 further defines a hole 308 therethrough to fluidly communicate the receptacle 306 with a pump. The receptacle 306 further defines a bottom hole 310. Liquid is drained out of the receptacle 306 through the bottom hole 310. The base 110 further includes a waste water outlet port 410 to drain waste water through a tube into the sink or other drain.

In another embodiment, the waste water is drained into the waste water tray 114. The waste water tray 114 receives waste liquid from the fluid reservoir 304. The waste water tray 114 is slidably received within the base 110. The drain pump 406 pumps waste liquid from the fluid reservoir 304 to the base 110. Waste liquid flows from the base 110 to the waste water tray 114.

As shown in FIG. 3B, the bottle cleaner 100 further includes an awning ring 314 disposed between the support frame 202 and the bottom liner 302. The awning ring 314 distributes the air inside the chamber to dry the bottles. The awning ring 314 also prevents water from entering an air flow channel 701 during washing.

Figure 4:
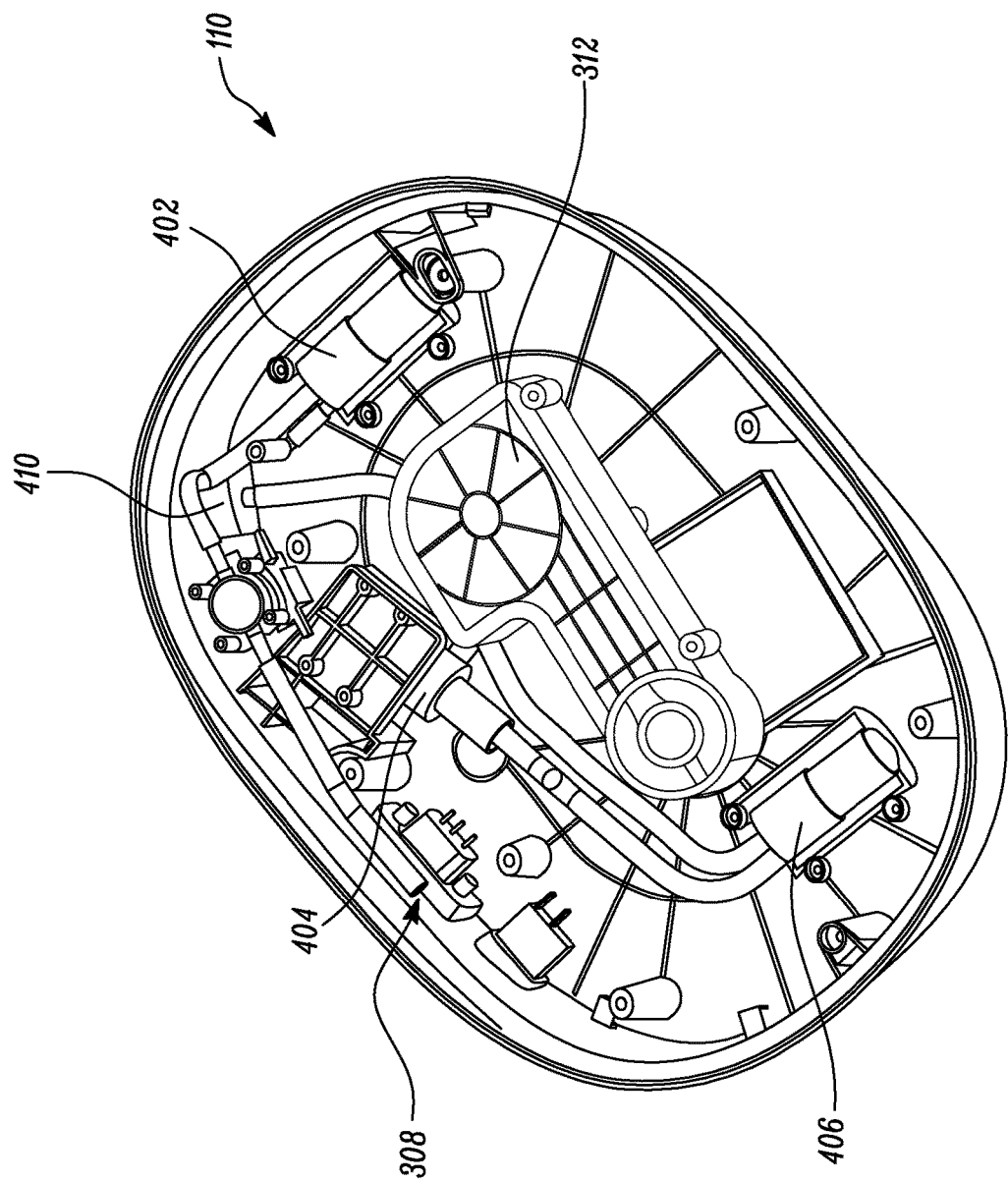
FIG. 4 shows internal parts of a base of the bottle cleaner, in accordance with the present invention.

FIG. 4 shows the internal components of the base 110. Referring to FIGS. 3 and 4, the bottle cleaner 100 includes at least one pump disposed within the base 110. The at least one pump pumps liquid from within the fluid reservoir 304 to one or more spray jets 601 for cleaning the bottles. The at least one pump includes a fresh-water pump 402, a sprinkler pump 404, and a drain pump 406. The fresh-water pump 402 receives liquid from the liquid tank 112. The liquid received from the liquid tank 112 is pumped into the receptacle 306 by the fresh-water pump 402. The receptacle 306 further defines the hole 308 therethrough to fluidly communicate the receptacle 306 with the fresh-water pump 402. The hole 308 is defined towards top of the receptacle 306. Liquid is drained out of the receptacle 306 through the bottom hole 310.

The bottle cleaner 100 further includes a blower 312 provided within the base 110. The blower 312 discharges air into the chamber through the plurality of openings 303. The blower may also be provided with a heater to increase air temperature and reduce drying time. The base 110 of the bottle cleaner 100 further includes the waste water outlet port 410. The waste water outlet port 410 allows the fluid to exit from the waste water drainage port 218.

Figure 5:
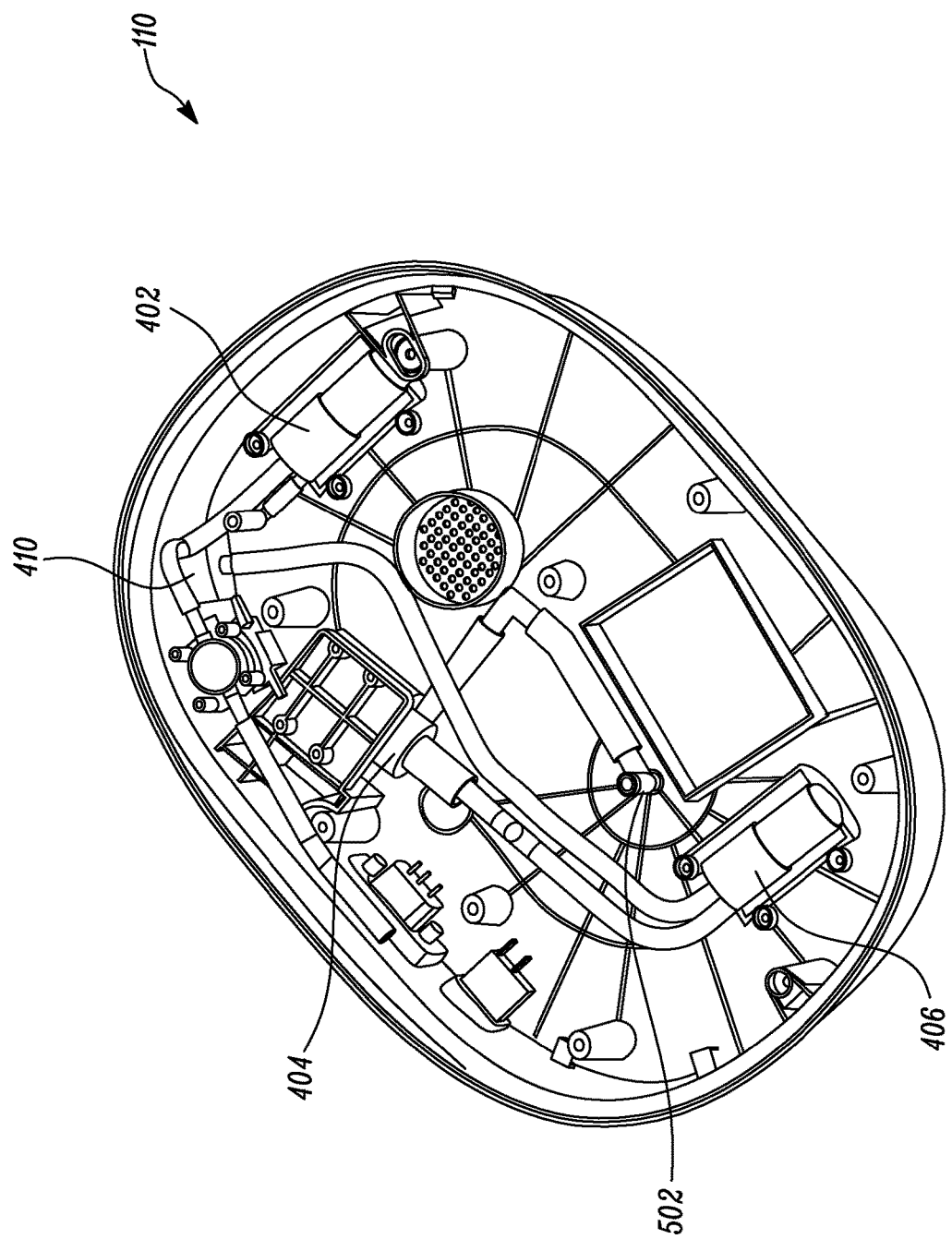
FIG. 5 shows internal parts of the base of the bottle cleaner without a blower, in accordance with the present invention.

FIG. 5 shows the bottle cleaner 100 without the blower 312. The liquid drained from the receptacle 306 is received by the sprinkler pump 404. The sprinkler pump 404 provides liquid to a sprinkler inlet 502.

Figure 6:
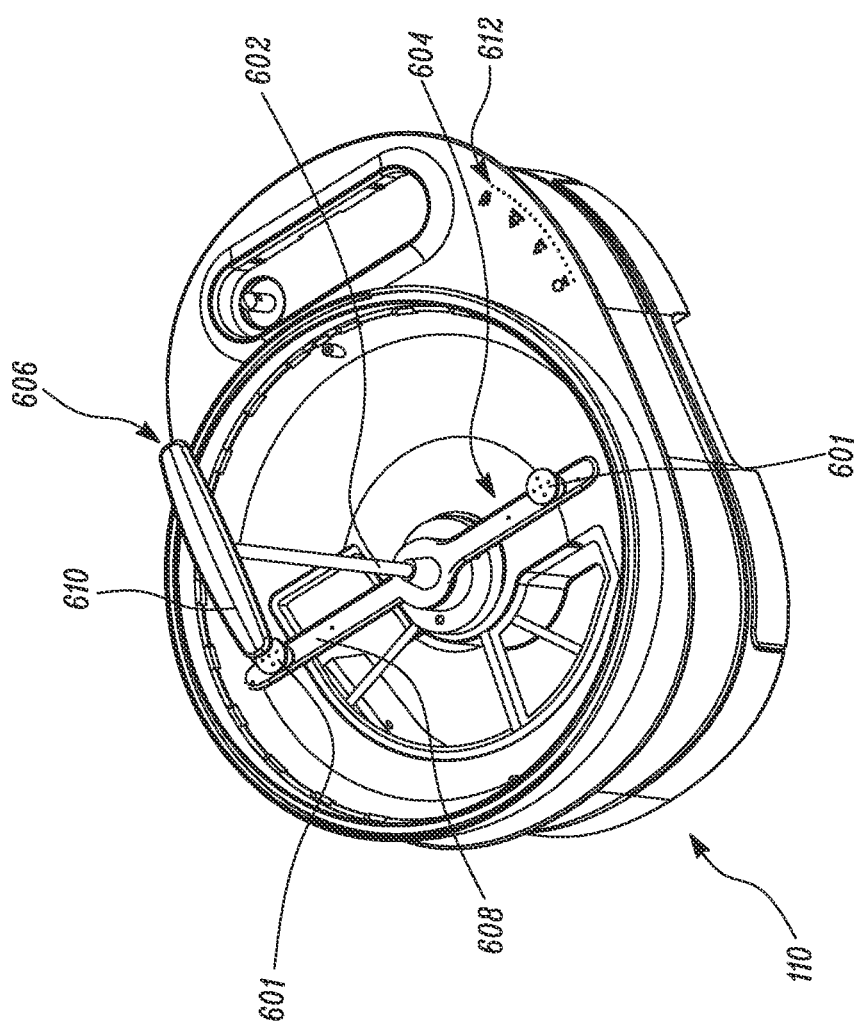
FIG. 6 shows a sprinkler of the bottle cleaner, in accordance with the present invention.

FIG. 6 shows details of a sprinkler system of the bottle cleaner 100. Referring to FIGS. 3-6, the bottle cleaner 100 includes a central tube 602 receiving liquid from the fluid reservoir 304 through the sprinkler pump 404. The bottle cleaner 100 further includes a bottom sprinkler assembly 604 and a top sprinkler assembly 606. The central tube 602 has openings (not shown) for the bottom sprinkler assembly 604 and the top sprinkler assembly 606. The bottom sprinkler assembly 604 and the top sprinkler assembly 606 both receive liquid from the central tube 602. Each of the top and bottom sprinkler assemblies 604, 606 includes sprinkler arms 608, 610, respectively, that rotate due to flow and discharge of liquid through outlets in the sprinkler arms 608, 610.

The top sprinkler assembly 606 may be a rotating spray mechanism. The top sprinkler assembly 606 may comprise a rotating sprayer mounted about the central tube 602. The rotating sprayer may include a tubular member having a plurality of holes. The holes may be provided in rows extending longitudinally along an outer surface of the tubular member. The holes may extend outwardly through angled nozzles. The nozzles may be angled relative to the radial direction such that as water exits the nozzles, a rotational force is imparted to the tubular member. Therefore, as the water exits the holes in the tubular member, the tubular member is caused to rotate. Such arrangement may provide for rotating spray jets 601 within the housing 102 to clean items placed within the housing 102.

Figure 7:
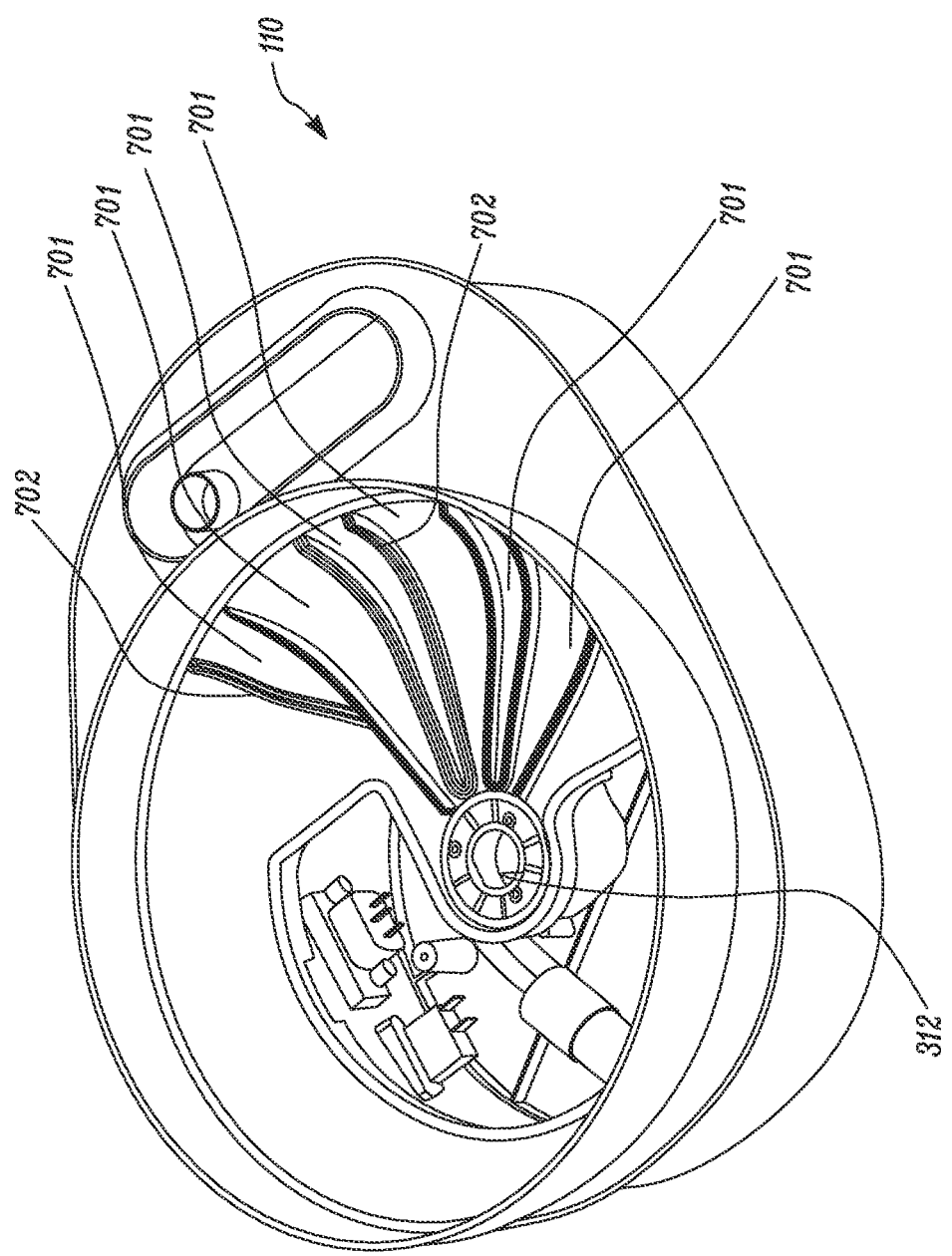
FIG. 7 shows guides for air flow, in accordance with the present invention.

FIG. 7 shows a partial cut away view of the bottle cleaner 100. Referring to FIGS. 3A-7, beneath the bottom liner 302, the bottle cleaner 100 includes baffles 702 for guiding air flow from the blower 312. The air exits from the blower 312 and flows along the baffles 702 beneath the bottom liner 302 and comes out from the plurality of openings 303. The baffles 702 may be defined in any suitable structural configuration. The present disclosure is not limited by the shape, size and structural configuration of the baffles 702.

With combined reference to FIGS. 1-7, for cleaning a bottle with the bottle cleaner 100, a user may open the lid 108 and place the bottle(s) within the chamber. Subsequently, the fresh-water pump 402 pumps clean liquid from the liquid tank 112. In an embodiment, the liquid is water. The fresh-water pump 402 provides the liquid to the receptacle 306 through the hole 308. The liquid in the receptacle 306 may be heated through the heater element 316 within the fluid reservoir 304 defined by the receptacle 306. Afterwards, the liquid exits from the bottom hole 310.

The bottle cleaner 100 may also be provided also with a control panel 612. The control panel 612 may be provided to control operation of the bottle cleaner 100. One or more pre-set programs may be provided. Such programs may include cleaning, sterilizing etc. The control panel 612 may have a plurality of buttons to control operations of the bottle cleaner 100. The control panel 612 may include buttons such as start operation, stop operation, drying, washing etc. The buttons may be functionally programmable to suit the needs of a particular user. Through the control panel, the bottle cleaner 100 may be activated to clean the bottles by an initial cleaning phase followed by a subsequent sterilization phase. Similarly, different activation programs may cause different type of cleaning actions to be performed.

In the cleaning phase, water is pumped from within the receptacle 306 via the bottom sprinkler assembly 604 and the top sprinkler assembly 606 to clean the bottles and other similar items placed within the bottle cleaner 100. During the sterilization phase, the heater element 316 is operated to release steam to the interior of the housing 102 to sterilize the items within the housing 102. In this way, bottles and other items can be conveniently washed and sterilized in a single operation in a convenient and portable device.

In an embodiment, the bottle cleaner 100 may also incorporate a drying phase. In this phase, only dry and warm air may be provided for drying the bottles after cleaning and sterilization. This phase may provide clean and dry bottles to the end user.

It will be readily apparent to persons skilled in the relevant arts that various modifications and improvements may be made to the foregoing embodiments, in addition to those already described, without departing from the basic inventive concepts of the present invention.

What is claimed is:

1. A bottle cleaner comprising:
a housing defining a chamber therein;
a support frame disposed within the housing to support one or more bottles;
a base disposed below the housing;
a bottom liner at least partially received within the housing, the bottom liner defining a plurality of openings and a fluid reservoir;
at least one pump disposed within the base to pump liquid from within the fluid reservoir to one or more spray jets for cleaning the bottles; and
a blower disposed within the base, the blower configured to discharge air into the chamber through the plurality of openings,
wherein the support frame comprises a tray pillar, a bottom tray disposed around the tray pillar and configured to support the one or more bottles, and a top tray disposed around the tray pillar, and
wherein the bottom tray comprises a plurality of circular members and a plurality of protrusions extending radially inwards from each circular member to accommodate different bottle sizes.

2. The bottle cleaner of claim 1, wherein the at least one pump includes a fresh-water pump, a sprinkler pump, and a drain pump.

3. The bottle cleaner of claim 1, wherein the housing comprises a top cover, a bottom cover and a lid movable relative to the top cover.

4. The bottle cleaner of claim 1, wherein the bottom tray further comprises a plurality of curved members attached to the plurality of circular members, each curved member comprising a plurality of studs.

5. The bottle cleaner of claim 4, wherein the bottom tray is rotatable about the tray pillar to allow easy loading of bottles.

6. The bottle cleaner of claim 1, further comprising a central tube receiving liquid from the fluid reservoir, a bottom sprinkler assembly receiving liquid from the central tube, and a top sprinkler assembly receiving liquid from the central tube.

7. The bottle cleaner of claim 1, wherein the bottom liner further comprises a receptacle that is at least partially received by the base, the receptacle defining the fluid reservoir, and wherein a heater element is received within the receptacle to heat liquid within the fluid reservoir.

8. The bottle cleaner of claim 7, wherein the receptacle further defines a hole therethrough to fluidly communicate the receptacle with the pump.

9. The bottle cleaner of claim 1, wherein the base further comprises a waste water outlet port on the back of the base to drain waste water through a tube to a sink or other drain.

10. The bottle cleaner of claim 1, wherein the base further comprises a waste tank configured to receive waste liquid from the fluid reservoir, the waste tank slidably received within the base to enable the device to be used when a sink or drain is not accessible.

11. The bottle cleaner of claim 1, further comprising a liquid tank disposed on the base, the liquid tank supplying liquid to the pump.

12. The bottle cleaner of claim 1, wherein the plurality of openings is circumferentially disposed on the bottom liner to direct air within the chamber in a circular flow to dry the bottles.

13. The bottle cleaner of claim 1, wherein the blower includes a heater to increase air temperature and reduce drying time.

14. A bottle cleaner comprising:
- a housing defining a chamber therein;
- a support frame disposed within the housing to support one or more bottles;
- a base disposed below the housing;
- a bottom liner at least partially received within the housing, the bottom liner defining a plurality of openings and a fluid reservoir;
- at least one pump disposed within the base to pump liquid from within the fluid reservoir to one or more spray jets for cleaning the bottles;
- a blower disposed within the base, the blower configured to discharge air into the chamber through the plurality of openings; and
- an awning ring disposed between the support frame and the bottom liner, wherein the awning ring is adapted to:
    - distribute the air inside the chamber to dry the bottles, and
    - prevent water from entering an air flow channel during washing.

* * * * *